US012788334B2

(12) United States Patent
Slomka et al.

(10) Patent No.: US 12,788,334 B2
(45) Date of Patent: Nov. 10, 2026

(54) AUTOMATED NONLINEAR REGISTRATION IN MULTI-MODALITY IMAGING

(71) Applicant: CEDARS-SINAI MEDICAL CENTER, Los Angeles, CA (US)

(72) Inventors: Piotr Slomka, Los Angeles, CA (US); Ananya Singh, Los Angeles, CA (US); Aditya Killekar, Beverly Hills, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 203 days.

(21) Appl. No.: 18/629,260

(22) Filed: Apr. 8, 2024

(65) Prior Publication Data

US 2024/0335174 A1 Oct. 10, 2024

Related U.S. Application Data

(60) Provisional application No. 63/457,517, filed on Apr. 6, 2023.

(51) Int. Cl.
*G06K 9/00* (2022.01)
*A61B 6/00* (2006.01)
(Continued)

(52) U.S. Cl.
CPC .............. *A61B 6/037* (2013.01); *A61B 6/504* (2013.01); *A61B 6/5205* (2013.01); (Continued)

(58) Field of Classification Search
CPC ....... A61B 6/037; A61B 6/504; A61B 6/5205; A61B 6/5288; A61B 6/5235; A61B 6/503;
(Continued)

(56) References Cited

U.S. PATENT DOCUMENTS

2008/0118132 A1* 5/2008 Ubelhart ................ A61B 6/032 382/131
2016/0183890 A1* 6/2016 Nathan ................ A61B 6/4417 378/9

(Continued)

OTHER PUBLICATIONS

Bebbington et al. ("Lesion detection in 18F-sodium fluoride bone imaging: a comparison of attenuation-corrected versus nonattenuation-corrected PET reconstructions from modern PET-CT systems", Nuclear Medicine Communications, 2022, 43(1), one page. (Year: 2022).*

(Continued)

*Primary Examiner* — Duy M Dang
(74) *Attorney, Agent, or Firm* — NIXON PEABODY LLP

(57) ABSTRACT

Automatic registration of multi-modal coronary imaging data is disclosed. First imaging data acquired using a first modality (e.g., positron emission tomography (PET) imaging) is applied to a neural network to output pseudo imaging data that is associated with a second modality (e.g., computed tomography (CT) imaging). The pseudo imaging data is then compared with (e.g., via nonlinear diffeomorphic registration) second imaging data acquired using the second modality to generate transformation information. This transformation information can then be applied to the first imaging data or other imaging data acquired in the first modality to register that imaging data with the second imaging data or other imaging data acquired in the second modality.

19 Claims, 10 Drawing Sheets

(51) Int. Cl.
*A61B 6/03* (2006.01)
*A61B 6/50* (2024.01)
*G06T 7/00* (2017.01)

(52) U.S. Cl.
CPC .......... *A61B 6/5288* (2013.01); *G06T 7/0012* (2013.01); *G06T 2207/20081* (2013.01); *G06T 2207/20084* (2013.01)

(58) Field of Classification Search
CPC ....... A61B 6/032; A61B 6/481; A61B 6/4417; G06T 7/0012; G06T 2207/20081; G06T 2207/20084; G06T 3/14; G06T 3/147; G06T 2207/10; G06T 2207/10072; G06T 2207/10081; G06T 2207/10104; G06V 101/22; G06V 10/10; G06V 10/82
See application file for complete search history.

(56) References Cited

U.S. PATENT DOCUMENTS

| | | | | |
|---|---|---|---|---|
| 2020/0085382 | A1* | 3/2020 | Taerum | A61B 5/055 |
| 2020/0184660 | A1* | 6/2020 | Shi | G06T 7/30 |
| 2021/0304402 | A1* | 9/2021 | Morgas | G06N 20/00 |

OTHER PUBLICATIONS

Ahuja et al. ("18F-Sodium Fluoride PET: History, Technical Feasibility, Mechanism of Action, Normal Biodistribution, and Diagnostic Performance in Bone Metastasis Detection Compared with Other Imaging Modalities", Journal of Nuclear Medicine Technology (JNMT) 2020, 48: 9-16 (Year: 2020).*

* cited by examiner

600

700

800

900

AUTOMATED NONLINEAR REGISTRATION IN MULTI-MODALITY IMAGING

PRIORITY CLAIM

This disclosure claims the benefit of and priority to U.S. Provisional Application No. 63/457,517, filed on Apr. 6, 2023. The contents of that application are hereby incorporated by reference in their entirety.

CROSS-FEDERALLY SPONSORED RESEARCH AND DEVELOPMENT

This invention was made with government support under Grant No. HL135557 awarded by the National Institutes for Health. The government has certain rights in the invention.

TECHNICAL FIELD

The present disclosure relates to medical imaging generally and more specifically to multi-modality imaging.

BACKGROUND

Modern medical professionals can make use of various different medical imaging modalities, each of which can provide different types of useful information. Computed tomography (CT) imaging is a technique that involves generating a three-dimensional image based on a series of x-ray images. CT can be performed with or without contrast. In coronary medicine, non-contrast CT scans can be useful to obtain information about how a patient's body causes attenuation for attenuation correction (AC) purposes. This CTAC data can then be used to make adjustments to other imaging data (e.g., imaging data of other modalities) to account for that patient's unique attenuation. In some cases, with-contrast CT scans can also be useful in coronary imaging. CT angiography (CTA) is a medical imaging technique that involves acquiring CT imaging data of a patient that has been injected with an appropriate dye, resulting in a visualization of the patient's vasculature. A coronary CTA (CCTA) is a special type of CTA that can be used to assess the vasculature of a patient's heart.

Positron emission tomography (PET) is an imaging technique that involves injection of a radiotracer that emits positrons that, when annihilated by contact with nearby electrons, generate photons travelling in opposite directions, which can then be detected by specialized equipment. PET has historically not been used very frequently for cardiac imaging. Some PET techniques, such as coronary $^{18}$F-sodium-fluoride ($^{18}$F—NaF) PET, have been found to be useful in visualizing atherosclerotic plaque and generating quantitative measurements (e.g., microcalcification activity). Often, obtaining useful information from PET imaging data requires co-registered CT imaging data. For example, non-contrast CT AC data can be used to correct for attenuation in co-registered PET imaging data. As another example, co-registration of PET imaging data with CTA imaging data may enable precise anatomical localization of the $^{18}$F—NaF activity within coronary plaques based on the anatomical information from the CTA imaging data.

Sometimes, PET and CT imaging data can be acquired on a single machine. However, even when acquired on a single machine during a single imaging session, misregistration can occur for various reasons, such as due to patient repositioning and the respiratory phase at which the CT imaging data is acquired.

Presently, co-registration of PET and CT imaging data is a time consuming and subjective process, often requiring great operator expertise. Operators must often rely on somewhat vague landmarks that may not easily translate from one modality to the other and must be able to register the imaging data in three dimensions. Traditional registration techniques involve first identifying and aligning a blood pool, identifying and aligning the aortic wall, and identifying and aligning more detailed landmarks, such as landmarks around coronary arteries and aortic and mitral valves. Even with experienced operators, manual registration errors can occur.

Thus, there is a need for system that allows efficient automated co-registration of PET and CT imaging data. There is a further need for a system that incorporates PET and CT data in cardiac imaging.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, supplemented by this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure include a computer-implemented method comprising receiving first imaging data of a subject. The first imaging data is acquired using a first imaging modality. The method further includes applying the first imaging data to a neural network trained to output pseudo imaging data. The pseudo imaging data can be associated with a second imaging modality. The method further includes receiving second imaging data of the subject. The second imaging data acquired using the second imaging modality. The method further includes receiving transformation information based at least in part on the pseudo imaging data and the received second imaging data. The method further includes applying the transformation information to a first set of imaging data associated with the first imaging modality to register the first set of imaging data to a second set of imaging data associated with the second imaging data.

Another example embodiment of the method is where the first modality imaging data is the first imaging data and the second modality imaging data is the second imaging data. In another embodiment, the first imaging modality is positron emission tomography (PET) and the second imaging modality is computed tomography (CT). In another embodiment, the second imaging data is non-contrast computed tomography attenuation correction imaging data. In another embodiment, the first imaging data is $^{18}$F—Na—F positron emission tomography imaging data. In another embodiment, the $^{18}$F—Na—F positron emission tomography imaging data is non-attenuation-corrected $^{18}$F—Na—F positron emission tomography imaging data. In another embodiment, the first modality imaging data is attenuation corrected $^{18}$F—Na—F positron emission tomography imaging data. In another embodiment, the second modality imaging data is computed tomography angiography imaging data. In another embodiment, the subject includes coronary tissue. In another embodiment, receiving the transformation information includes generating the transformation information by applying a diffeomorphic registration algorithm to the pseudo imaging data and the second imaging data. In another embodiment, the diffeomorphic registration algorithm is a demons algorithm. In another embodiment, the neural network includes a generator neural network of a generative adversarial network (GAN). The generator neural network is trained to receive first training data associated with the first imaging modality as input and output generated imaging data associated with the second imaging modality. In another embodiment, the GAN is a conditional GAN having at least one condition. The at least one condition is a slice label associated with the training data. Each image slice of the training data is associated with a respective slice label. In another embodiment, the neural network includes skip connections with attention gates connecting one or more encoder layers with one or more corresponding decoder layers. In another embodiment, applying the first imaging data to the neural network to output the pseudo imaging data includes individually applying image slices of the first imaging data to the neural network to output corresponding pseudo imaging slices of the pseudo imaging data. In another embodiment, the example method includes receiving third imaging data of the subject, the third imaging data acquired using the second imaging modality; and generating additional transformation information based at least in part on a comparison of the second imaging data and the third imaging data. Registering the first modality imaging data with the second modality imaging data further includes applying the additional transformation information. The second modality imaging data is the third imaging data. In another embodiment, the first imaging data is nonattenuation corrected positron emission tomography imaging data. The second imaging data is non-contrast computed tomography attenuation correction imaging data. The third imaging data is computed tomography angiography imaging data. In another embodiment, the example method further includes receiving fourth imaging data of the subject, the fourth imaging data acquired using the first imaging modality. The first modality imaging data is the fourth imaging data. In another embodiment, the fourth imaging data is attenuation corrected positron emission tomography imaging data. In another embodiment, the example method further includes identifying one or more regions of interest of the subject based at least in part on the second modality imaging data; and generating a quantification measurement based at least in part on the first modality imaging data and the identified one or more regions.

Embodiments of the present disclosure include a system. The system comprises one or more data processors. The system further comprises a non-transitory computer-readable storage medium containing instructions which, when executed on the one or more data processors, cause the one or more data processors to perform the method(s) described above.

Embodiments of the present disclosure include a computer-program product tangibly embodied in a non-transitory machine-readable storage medium, including instructions configured to cause a data processing apparatus to perform the method(s) described above.

BRIEF DESCRIPTION OF THE DRAWINGS

The specification makes reference to the following appended figures, in which use of like reference numerals in different figures is intended to illustrate like or analogous components.

DETAILED DESCRIPTION

Figure 1:
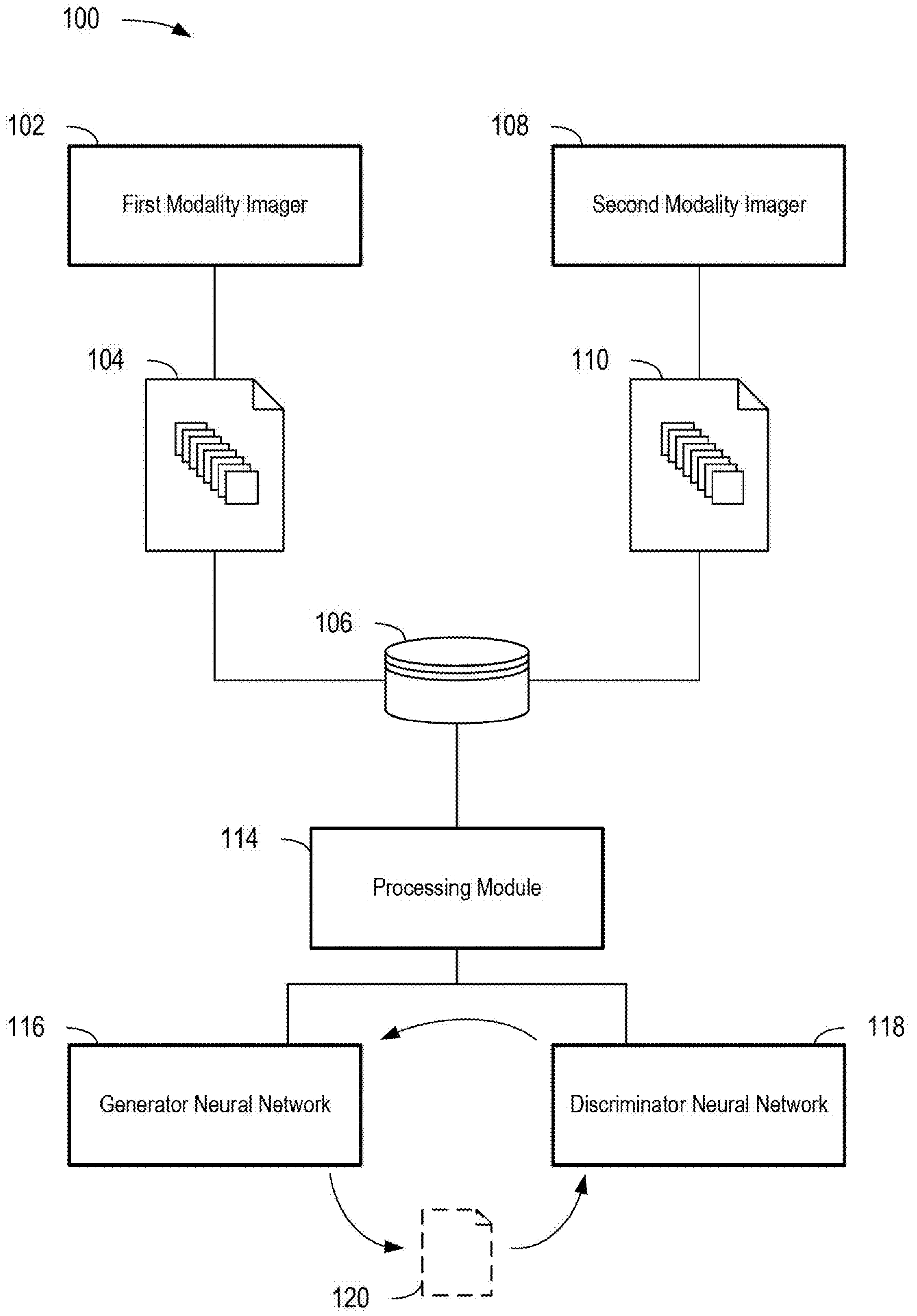
FIG. 1 is a schematic diagram depicting a computing environment for training a neural network, according to certain aspects of the present disclosure.

Certain aspects and features of the present disclosure relate to automatic registration of multi-modal coronary imaging data. First imaging data acquired using a first modality (e.g., positron emission tomography (PET) imaging) is applied to a neural network to output pseudo imaging data that is associated with a second modality (e.g., computed tomography (CT) imaging). The pseudo imaging data is then compared with (e.g., via nonlinear diffeomorphic registration) second imaging data acquired using the second modality to generate transformation information. The transformation information can then be applied to the first imaging data or other imaging data acquired in the first modality to register that imaging data with the second imaging data or other imaging data acquired in the second modality.

In an example, non-attenuation corrected PET image slices can be used to generate pseudo-CT image slices. The pseudo-CT image slices can be registered to non-contrast CT attenuation correction image slices using diffeomorphic non-rigid registration, resulting in first transformation information. The non-contrast CT attenuation correction image slices can be registered to CT angiography image slices using rigid registration, resulting in second transformation information. The first and second transformation information can then be applied together to attenuation corrected PET image slices to register the attenuation corrected PET images slices to the CT angiography image slices.

In some cases, imaging data from a first modality can provide certain useful information when co-registered with imaging data from another modality. Information provided by the imaging data of one modality can then be used to interpret or otherwise affect the imaging data from the other modality. For example, $^{18}$F—Na—F PET imaging data must be co-registered with CTA imaging data to obtain certain information, such as accurate quantification of PET activity, which can depend on the anatomical information derived from the CTA imaging data.

As used herein, the term imaging data is inclusive of any data usable to recreate or represent 2-D or 3-D images acquired using the given modality. In some cases, imaging data can include image data (e.g., data usable to recreate or represent 2-D or 3-D images) and ancillary data (e.g., additional information associated with a given imaging study, such as demographic information about the patient from whom the images are acquired). For example, PET imaging data can include a single 2-D image slice (e.g., information about a 2-dimensional collection of pixels), multiple 2-D images slices, 3D image volume information (e.g., information about a 3-dimensional collection of voxels), and the like. In some cases, imaging data can include imaging data from one or more time periods.

According to certain aspects of the present disclosure, an automated method for co-registering imaging data from different modalities (e.g., PET imaging data and CTA imaging data) makes use of a conditional generative adversarial network (cGAN) and a diffeomorphic nonlinear registration algorithm.

The GAN can involve a first neural network (e.g., a generator network) that outputs generated data and a second neural network (e.g., a discriminator network) that determines if the generated data is realistic (e.g., whether the provided data is real data or generated data). These networks are trained together until the first neural network is able to create sufficiently realistic generated data with sufficient reliability (e.g., when the discriminator network is no longer able to discriminate real data from generated data). GANs can be used for generation and translation of image data with the objective of learning the underlying distribution of source domain to generate indistinguishable target realistic data samples.

Certain aspects of the present disclosure involve using a GAN to generate "pseudo-CT" imaging data from corresponding PET data. In some cases, the PET data used for generation of the pseudo-CT imaging data is non-attenuation corrected (NAC) PET data. In some cases, the use of NAC PET data can be especially useful as it is immune to potential misregistration of emission data and non-contrast CT AC images, which can affect PET AC reconstructions.

The generated pseudo-CT imaging data is naturally perfectly aligned to the PET imaging data, as it is derived from the PET imaging data, unlike the actual non-contrast CT, which must be separately acquired and is thus prone to misalignment (e.g., misalignment due to patient motion even if acquired during the same imaging session). The pseudo-CT imaging data can then be nonlinearly registered to actual CT imaging data using a diffeomorphic registration algorithm, which can iteratively compute the displacement for each voxel in a computationally efficient manner. The resulting transformation information can then be used for PET to CT registration (e.g., can be applied to the PET imaging data to register it with the actual CT imaging data).

In some cases, registration of the pseudo-CT imaging data to actual CT imaging data can involve registering the pseudo-CT imaging data to non-contrast CT attenuation correction imaging data.

In coronary artery disease, $^{18}$F—NaF uptake acquired from PET scanning provides an assessment of disease activity and prediction of subsequent disease progression and clinical events. Novel uptake measures such as coronary microcalcification activity (CMA) enable a patient-level assessment of disease activity, which is guided by centerlines derived from contrast-enhanced CT angiography. However, proper analysis of the PET imaging data can require that it be registered to the CT angiography imaging data.

Certain aspects and features of the present disclosure relate to the challenging task of fully automated coronary PET and CT angiography image registration. Automatic registration of PET and CT angiography is difficult to accomplish due to nonlinear respiratory and cardiac motion displacement between the two modalities, as well as limited anatomical information provided by coronary PET. Certain aspects and features of the present disclosure leverage the fact that the generated pseudo-CT is perfectly registered to PET, which is the input to a GAN, unlike the non-contrast CT attenuation correction image acquired in the same imaging session. The latter misalignment occurs due to patient motion and the lengthy PET acquisition. By registering the pseudo-CT to the actual CT and then subsequently to CT angiography with nonlinear diffeomorphic registration, these issues are overcome, and the transform to register PET to CT angiography is obtained.

Automatic GAN-based nonlinear diffeomorphic registration of PET and CT angiography can be employed for accurate alignment of images. This method facilitates automated analysis of $^{18}$F—NaF coronary uptake with the user input limited to careful inspection whether extra-coronary activity does not corrupt the coronary $^{18}$F—NaF uptake measurements. In view of the already available tools for quantification of $^{18}$F—NaF activity on a per-vessel and per-patient level, automatic PET to CT angiography registration as disclosed herein enables the more widespread use of coronary PET.

Additionally, certain aspects of the present disclosure could further simplify the complex processing protocols needed for clinical application of coronary PET imaging.

The use of a GAN to create pseudo imaging data that is then used for nonlinear diffeomorphic registration is especially useful for PET to CT registration. Since $^{18}$F—NaF coronary PET imaging does not visualize the myocardium, direct PET to CT angiography registration is currently not feasible, even with the use of convolution neural networks that attempt to non-rigidly register PET and CT imaging data. Certain aspects of the present disclosure overcome the difficulties in image registration of images with different visual appearances.

Certain aspects and features of the present disclosure improve how imaging analyzing computer systems operate by providing a fully automated method of registering multimodal imaging data that can register imaging data much faster and more accurately than manual registration by trained experts. Further, the automatic registration allows for $^{18}$F—NaF CMA uptake values to be available as soon as image reconstruction is completed and CT angiography coronary centerlines are available, rather than having to wait for an expert to receive, review, and register the imaging data.

Certain aspects and features of the present disclosure effect a particular treatment or prophylaxis for a disease or medical condition such as cardiac disease. For example, in some cases, certain aspects of the present disclosure can provide an accurate and fast registration of PET imaging data with CT imaging data, which can provide better and faster quantitative results from analysis of the PET imaging data based on volumes of interest defined by the CT imaging data. These quantitative results can provide a clinician with advanced notice of when to begin treatment or take other actions to protect against major cardiac events for a patient.

Certain aspects and features of the present disclosure are closely integrated in and provide significant benefits to a specific field of technology of coronary scanning. For example, the interpretation of coronary PET scan data based on volumes of interest defined by CT imaging data is performed. While manual registration of PET imaging data with CT imaging data has existed in the past, those manual techniques are very time-consuming, are prone to user error and misregistration, and require trained experts to perform the registration. By contrast, certain aspects and features of the present disclosure allow for the practical advantages of automatic registration of PET imaging data with CT imaging data in very fast speeds (e.g., approximately 33 times faster than manual, expert registration), with minimal to no error, and without the need for trained experts to perform the registration.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative embodiments but, like the illustrative embodiments, should not be used to limit the present disclosure. The elements included in the illustrations herein may not be drawn to scale.

FIG. 1 is a schematic diagram depicting a computing environment 100 for training a neural network, according to certain aspects of the present disclosure. Specifically, the computing environment 100 can include the training of a generator neural network 116, which may include training of a discriminator neural network 118. Together, the generator neural network 116 and discriminator neural network 118 can operate as a generative adversarial network (GAN).

The computing environment 100 can make use of imaging data from at least a first modality imager 102 and a second modality imager 108. While any suitable imagers can be used, in at least some cases, the first modality imager 102 is a PET imager and the second modality imager 108 is a CT imager. In some cases, the first modality imager 102 and second modality imager 108 are implemented together (e.g., in a single piece of equipment), such as for a PET/CT imager.

As used herein, the term modality is intended to indicate a particular method or procedure for acquiring imaging data. Imaging data of different modalities is generally acquired by different imaging devices (e.g., imagers), although that need not always be the case. Examples of different imaging modalities include PET imaging, CT imaging, ultrasound imaging, etc. Generally, imaging data that differs only due to the use of contrast or the use of similar machine settings would be considered as both being acquired from the same imaging modality. For example, non-contrast CT imaging data for attenuation correction purposes is considered as being acquired using the same imaging modality as CT angiography imaging data, which is acquired using contrast. As another example, non-attenuation corrected PET imaging data is considered as being acquired using the same imaging modality as attenuation corrected PET imaging data. However, non-contrast CT imaging data and CT angiography imaging data are both considered to be acquired using a different imaging modality than non-attenuation corrected and attenuation corrected PET imaging data.

The first modality imager 102 can generate first imaging data 104, which can include a series of two-dimensional images that can be analyzed using tomographic techniques to recreate a three-dimensional image of a subject (e.g., arteries of a heart and/or other coronary or cardiac related tissue).

The second modality imager 108 can generate second imaging data 110, which can include a series of two-dimensional images that can be analyzed using tomographic techniques to recreate a three-dimensional image of a subject (e.g., arteries of a heart and/or other coronary or cardiac related tissue). The second modality imager 108 uses a different imaging modality than the first modality imager 102.

The first imaging data 104 and the second imaging data 110 can be stored in a database 106. Database 106 can be implemented as a single database or multiple databases, and can be implemented on a single computing device or across multiple computing devices.

First imaging data 104 and second imaging data 110 can be collected from a single patient, optionally during a single imaging session. For example, a combination PET/CT scanner can be used to acquire both PET scans and CT scans of a patient's coronary arteries.

Imaging data collected across multiple patients over time can be compiled (e.g., in the database 106) and used as training data. This training data thus includes multiple sets of first imaging data 104 (e.g., PET imaging data, such as NAC PET imaging data) and second imaging data 110 (e.g., CT imaging data, such as non-contrast CT AC imaging data) from multiple imaging sessions.

A processing module 114 (e.g., one or more computers or other suitable data processing apparatuses) can use the training data (e.g., from the database 106) to train a neural network (e.g., generator neural network 116). While other neural networks may be used, generally a GAN is used, which involves the generator neural network 116 and the discriminator neural network 118.

The processing module 114 can control training of the generator neural network 116 and discriminator neural network 118. The processing module 114 can feed first imaging data 104 to the generator neural network to generate pseudo imaging data 120. Then, the processing module 114 can feed the pseudo imaging data 120 and the second imaging data 110 to the discriminator neural network 118 to generate a determination as to whether or not the pseudo imaging data 120 is real or generated. Progressively, the generator neural network 116 and discriminator neural network 118 can be trained until the discriminator neural network 118 is no longer able to distinguish the pseudo imaging data 120 from the second imaging data 110.

The result of the training performed in the computing environment 100 is the trained generator neural network 116, which can create realistic pseudo imaging data 120 from first imaging data 104. Because second imaging data 110 is fed to the discriminator neural network 118 during training, the generator neural network 116 is trained to output pseudo imaging data 120 that appears to have been acquired using the same modality as the second imaging data 110, which is the second modality.

In some cases, the first imaging data 104 and second imaging data 110 is provided to the generator neural network 116 and the discriminator neural network 118, respectively, one slice at a time. In such cases, the generator neural network 116 would take a single 2-dimensional image slice from the first imaging data 104 as an input and generate a corresponding pseudo image slice. Likewise, the discriminator neural network 118 would compare a corresponding 2-dimensional image slice of the second imaging data 110 with the generated pseudo image slice. In some cases, the generator neural network 116 and the discriminator neural network 118 can also take a slice identifier as an input, which can identify which slice of the first imaging data 104 and/or second imaging data 110 that is being provided. Thus, the GAN can be considered a conditional GAN based on the condition of the slice identifier.

In some cases, first imaging data 104 and/or second imaging data 110 can be preprocessed by the processing module 114 prior to being supplied to the generator neural network 116 and/or discriminator neural network 118. In an example, when the first imaging data 110 is PET imaging data and the second imaging data 110 is CT imaging data, preprocessing can involve resampling and resizing the CT image slices to the dimensions of the PET image slices, per patient. For generation of pseudo-CT imaging data, each slice of PET and CT imaging data can be normalized by subtracting with mean and dividing with the voxel range of Gaussian-smoothed patient data. In some cases, the image slices can be cropped using the largest CT image slice by automatically obtaining the bounding box using the boundary of the CT scan. The same bounding box can be applied to the corresponding PET imaging data. Generated pseudo-CT image slices can be combined and overlayed with the real-CT AC image to obtain the background.

The computing environment 100 can be implemented in a single location or across many locations. For example, many first modality imagers 102 and second modality imagers 108 from locations all over the world can be used to generate respective imaging data, which can be stored in disparate databases present in different locations.

Figure 2:
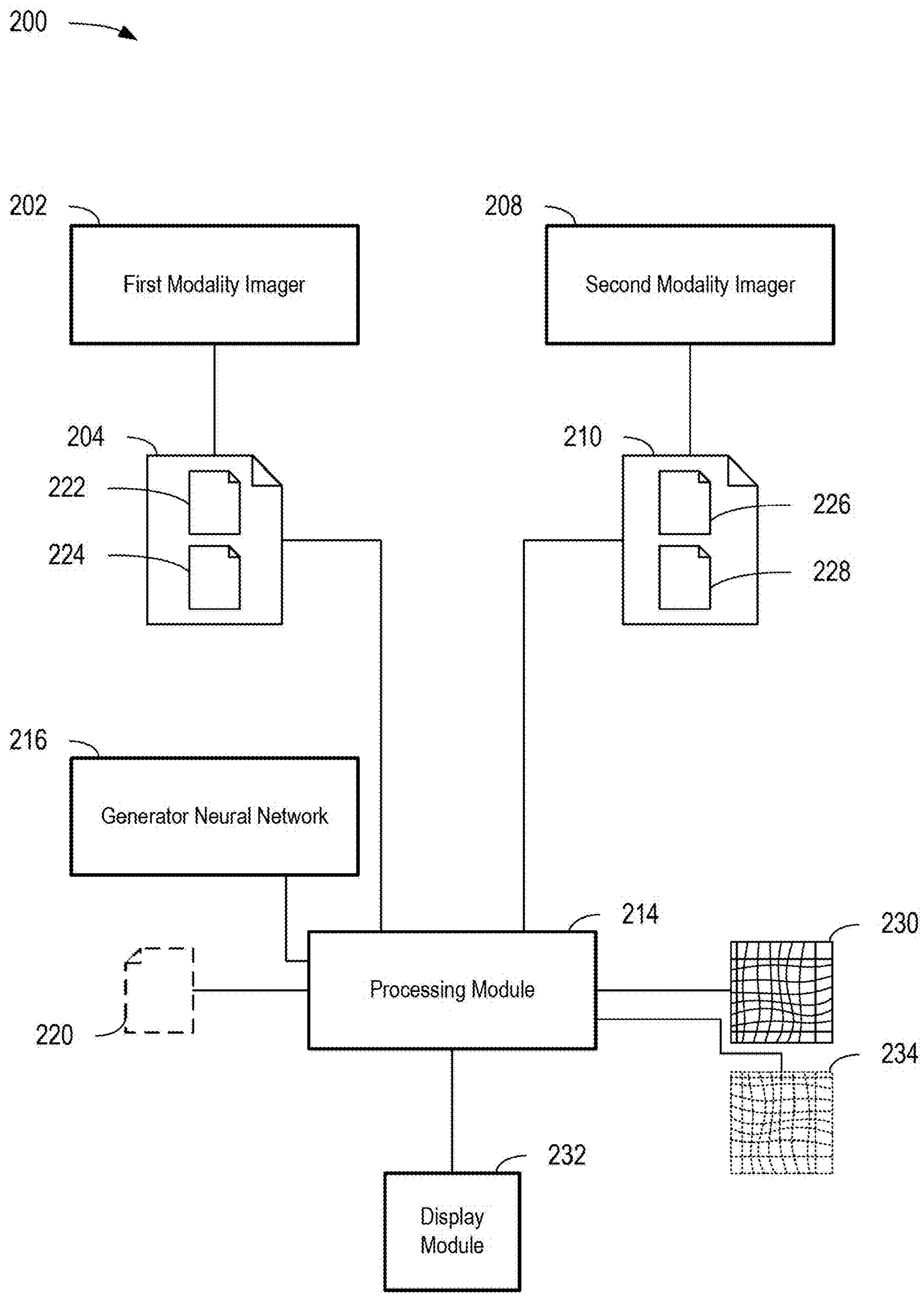
FIG. 2 is a schematic diagram depicting a computing environment for acquiring and processing imaging data, according to certain aspects of the present disclosure.

FIG. 2 is a schematic diagram depicting a computing environment 200 for acquiring and processing imaging data, according to certain aspects of the present disclosure. The computing environment 200 can include a first modality imager 202 and a second modality imager 208, which can be similar to the first modality imager 102 and second modality imager 108 of FIG. 1. For example, in some cases, the first modality imager 202 and second modality imager 208 can be integrated together and embodied in a single piece of hardware (e.g., a PET/CT scanner). The computing environment 200 can further include a processing module 214 and a display module 232. The computing environment 200 can include memory (not shown) that can house programming instructions, imaging data (e.g., first modality imaging data 204 and second modality imaging data 210), the generator neural network 220, pseudo imaging data 220, transformation information 230, or the like.

The imagers 202, 208, processing module 214, and display module 232 can be incorporated into a single housing or split into any number of housings, whether physically coupled together or not. The imagers 202, 208, processing module 214, and display module 232 can be located in a shared location (e.g., a room, suite, facility, or building) or in different locations. In some cases, the imagers 202, 208 can be located in a first location and the processing module 214 and display module 232 can be located in a separate, second location. For example, the imagers 202, 208 can be implemented as a combination PET/CT scanner located in a medical imaging facility and the processing module 214 and display module 232 can be a physician's computer workstation (e.g., the processor and display of the computer workstation) in the physician's office that is located in a separate facility, separate city, or even separate county as the medical imaging facility. Other combinations can occur.

The first modality imager 202 and second modality imager 208 can be any suitable imaging device for respectively generating first modality imaging data 204 and second modality imaging data 210 in a first imaging modality and second imaging modality, respectively. According to certain aspects and features of the present disclosure, the first modality imager 202 is a PET imager that acquires first modality imaging data 204 in the form of PET images, and the second modality imager 208 is a CT imager that acquires second modality imaging data 210 in the form of CT images.

The imagers 202, 208 can be communicatively coupled to the processing module 214 and/or the display module 232 via any suitable technique, such as wired or wireless connections, including direct connections or networked connections. In some cases, imagers 202, 208 can be coupled to processing module 214 via a network, such as a local area network, a wide area network, a cloud network, or the Internet. In some cases, data transfer between the imagers 202, 208 and the processing module 214 can occur via removable physical media, such as compact disks or flash drives.

The first modality imaging data 204 and second modality imaging data 210 can be stored and/or transferred in any suitable format. In some cases, the first modality imaging data 204 and second modality imaging data 210 can be stored and/or displayed as two-dimensional or three-dimensional images. In some cases, the first modality imaging data 204 and second modality imaging data 210 can be stored as a collection of data points or voxels.

The first modality imaging data 204 can include first imaging data 222 and optionally fourth imaging data 224. The second modality imaging data 210 can include second imaging data 226 and optionally third imaging data 228. In some cases, the first imaging data 222 is non-attenuation corrected PET imaging data and the second imaging data 226 is non-contrast CT AC imaging data. In some cases, the third imaging data 228 is CT angiography imaging data. In some cases, the fourth imaging data 224 is attenuation corrected PET imaging data.

The processing module 214 can be any suitable computing device for processing the first modality imaging data 204 and second modality imaging data 210 as disclosed herein. The processing module 214 can receive the first modality imaging data 204 and use that first modality imaging data 204 to create pseudo imaging data 220. The pseudo imaging data 220 can be created by accessing a generator neural network 216 and applying the first modality imaging data 204 to the generator neural network 216, which would then output the pseudo imaging data 220. The processing module 214 can receive the second modality imaging data 210 and perform a registration process to register the pseudo imaging data 220 to the second modality imaging data 210. As a result of this registration process, transformation information 230 can be created and stored. The processing module 214 can then apply the transformation information 230 to register the first modality imaging data 204 to the second modality imaging data 210.

In an example, the processing module 214 can take the first imaging data 222 and supply it to the generator neural network 216 to output pseudo imaging data 220, which is then registered to second imaging data 226 to create transformation information 230. In some cases, the processing module 214 can also register the second imaging data 226 to third imaging data 228 to create additional transformation information 234. The processing module 214 can then apply the transformation information 230 and additional transformation information 234 to the fourth imaging data 224 to register that fourth imaging data 224 with the third imaging data 228.

In some cases, in addition to automatically registering first modality imaging data 204 with second modality imaging data 210, the processing module 214 can generate output data. The output data can include visual representations of the first modality imaging data 204 and/or second modality imaging data 210, visual representations of the registration of the first modality imaging data 204 with the second modality imaging data 210, and/or quantitative measurements based on registered first modality imaging data 204 and second modality imaging data 210.

In some cases, the processing module 214 can include an input device, such as a computer mouse, keyboard, touchscreen, or the like. The input device can allow a user (e.g., a physician or other medical professional) to interact with the first modality imaging data 204 and second modality imaging data 210 and control the registration process and/or the generation of output data. In some cases, the processing module 214 can include the display module 232 for displaying first modality imaging data 204, second modality imaging data 210, output data 218, pseudo imaging data 220, transformation information 230, and/or the like. In some cases, the display module 232 is used in conjunction with or includes an input device.

Output data, once generated, can be presented on the display module 232 or otherwise presented to a user or patient. The output data, especially quantitative measurements such as SUVmax, TBRmax, and CMA, can be usable to help tailor a treatment plan for a patient.

Figure 3:
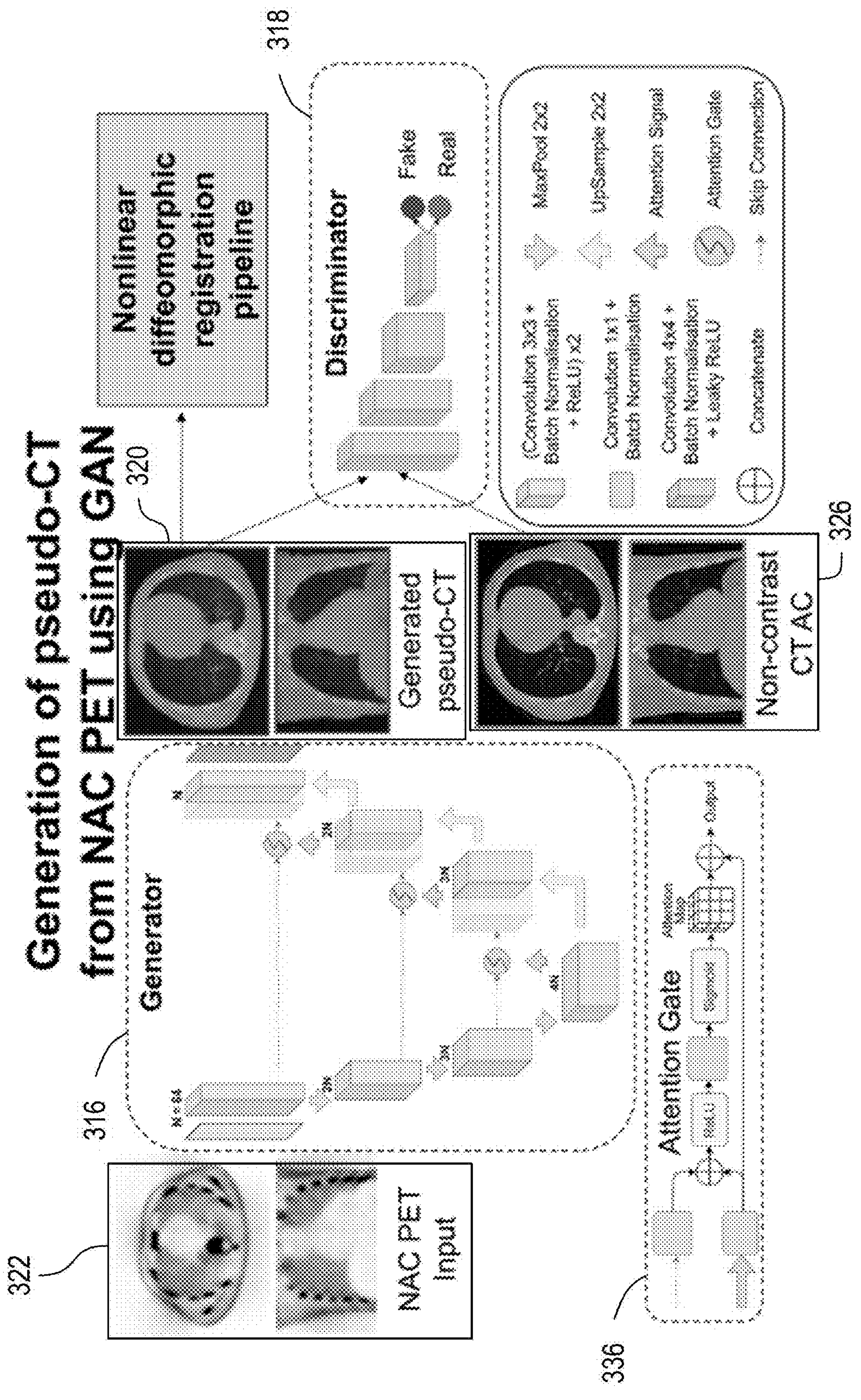
FIG. 3 is a schematic diagram depicting a neural network for generating pseudo imaging data, according to certain aspects of the present disclosure.

FIG. 3 is a schematic diagram depicting a neural network 316 for generating pseudo imaging data, according to certain aspects of the present disclosure. The generator neural network 316 can receive NAC PET imaging data 322 as an input and can output generated pseudo-CT imaging data 320. The generator neural network 316 can be trained as part of a GAN alongside a discriminator neural network 318. The discriminator neural network can receive as input the generated pseudo-CT imaging data 320 and corresponding non-contrast CT AC imaging data 326.

In some cases, the generator neural network 316 can be implemented as a modified UNet with skip connections and attention gates 336. The UNet is an encoder-decoder network that can be used to learn the information present in the input image and encapsulate it. In some cases, the encoder portion can include repeated convolution layers, each followed by a batch normalization and a rectified linear unit (ReLU) followed by a maxpool operation for dimension reduction. The decoder portion can upsample the information learned in a meaningful representation based on the condition of same slice of the second imaging data (e.g., the non-contrast CT AC imaging data 326 or the second imaging data 110 of FIG. 1).

In some cases, especially when the first imaging modality is PET, the generator neural network 316 can make use of skip connections with attention gates 336 to connect layers of the encoder with corresponding layers of the decoder to localize high-level salient features present in PET, but often lost in downsampling. Attention gates 336 can help suppress irrelevant background noise without the need of segmenting heart regions, and can preserve features relevant for CT generation. The output of attention can be concatenated with the corresponding upsampling block.

The discriminator neural network 318 can be implemented as a deep convolutional neural network (CNN) with two inputs: i) the pseudo imaging data (e.g., generated pseudo-CT imaging data 320) that was output from the generator neural network 316; and ii) corresponding second imaging data (e.g., non-contrast CT AC imaging data 326). For example, the discriminator neural network 318 can take as input a generated pseudo-CT image slice and a corresponding non-contrast CT AC image slice.

In some cases, the discriminator neural network 318 can be set up to take a 70×70 pixel patch of both inputs and estimate a similarity metric. The discriminator neural network 318 can repeat this process for the entire slice, averaging the similarities for each patch, to provide a single probability of whether the pseudo-CT slice was real or fake when compared to the CT AC image slice.

Figure 4:
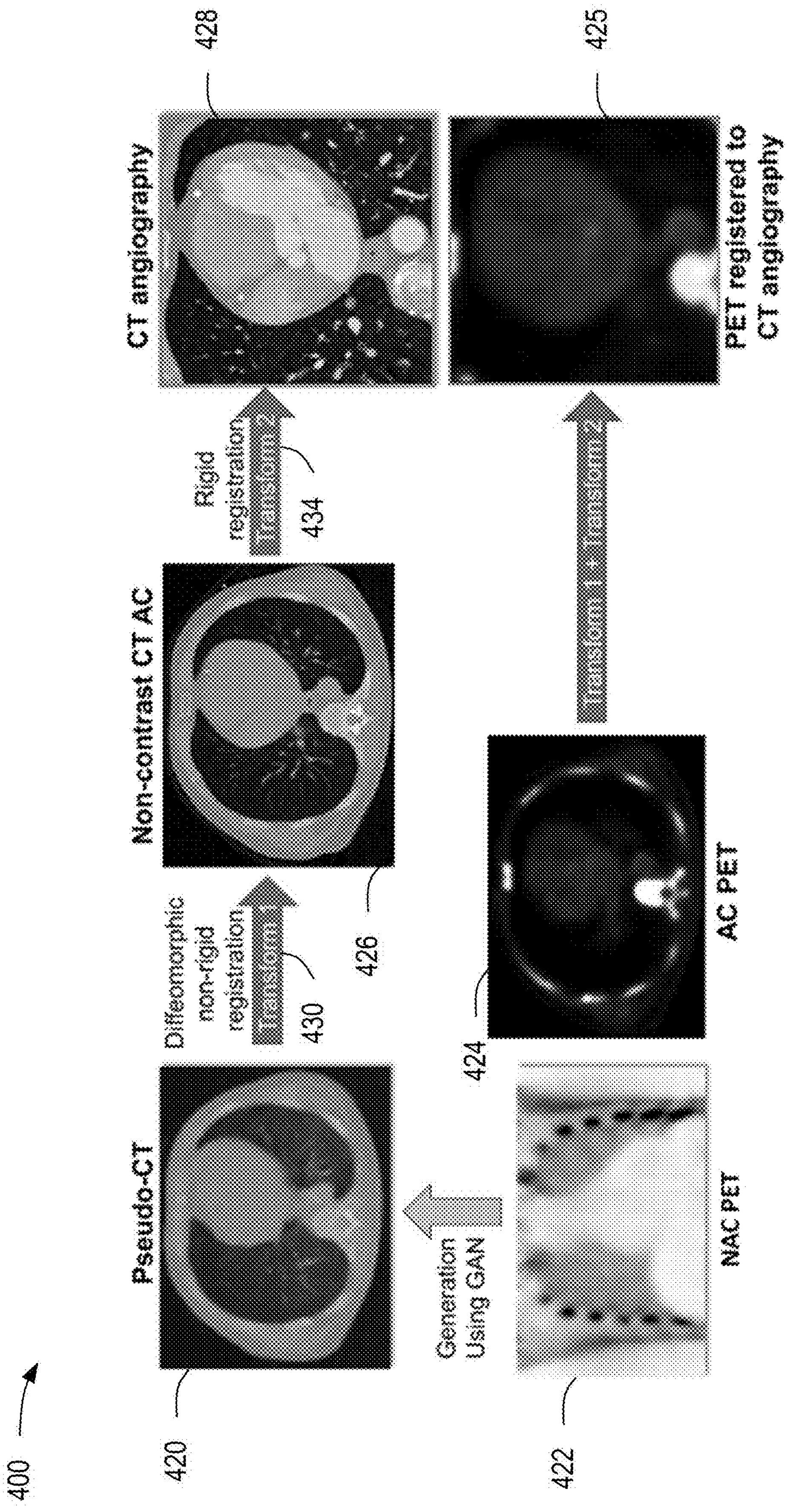
FIG. 4 is a schematic diagram depicting imaging data used for automatic multi-modal registration, according to certain aspects of the present disclosure.

FIG. 4 is a schematic diagram depicting imaging data 400 used for automatic multi-modal registration, according to certain aspects of the present disclosure. NAC PET imaging data 422 can be applied to a generator neural network (e.g., generator neural network 116 of FIG. 1) to generate pseudo-CT imaging data 420. The pseudo-CT imaging data 420 can then be registered to non-contrast CT AC imaging data 426 via diffeomorphic non-rigid registration. This registration process can result in first transformation information 430. Separately, the non-contrast CT AC imaging data 426 can be registered to CT angiography imaging data 428 via rigid registration. This registration process can result in second transformation information 434. Finally, attenuation corrected PET imaging data 424 can be registered to the CT angiography imaging data 428 via application of the first and second transformation information 430, 434, resulting in a PET registered to CT angiography 425.

While imaging modalities and types of imaging data are described in FIG. 4, in some cases other imaging modalities and/or other types of imaging data can be used. For example, in some cases NAC PET imaging data 422 can be registered to non-contrast CT AC imaging data 426 using only the first transformation information 430.

Figure 5:
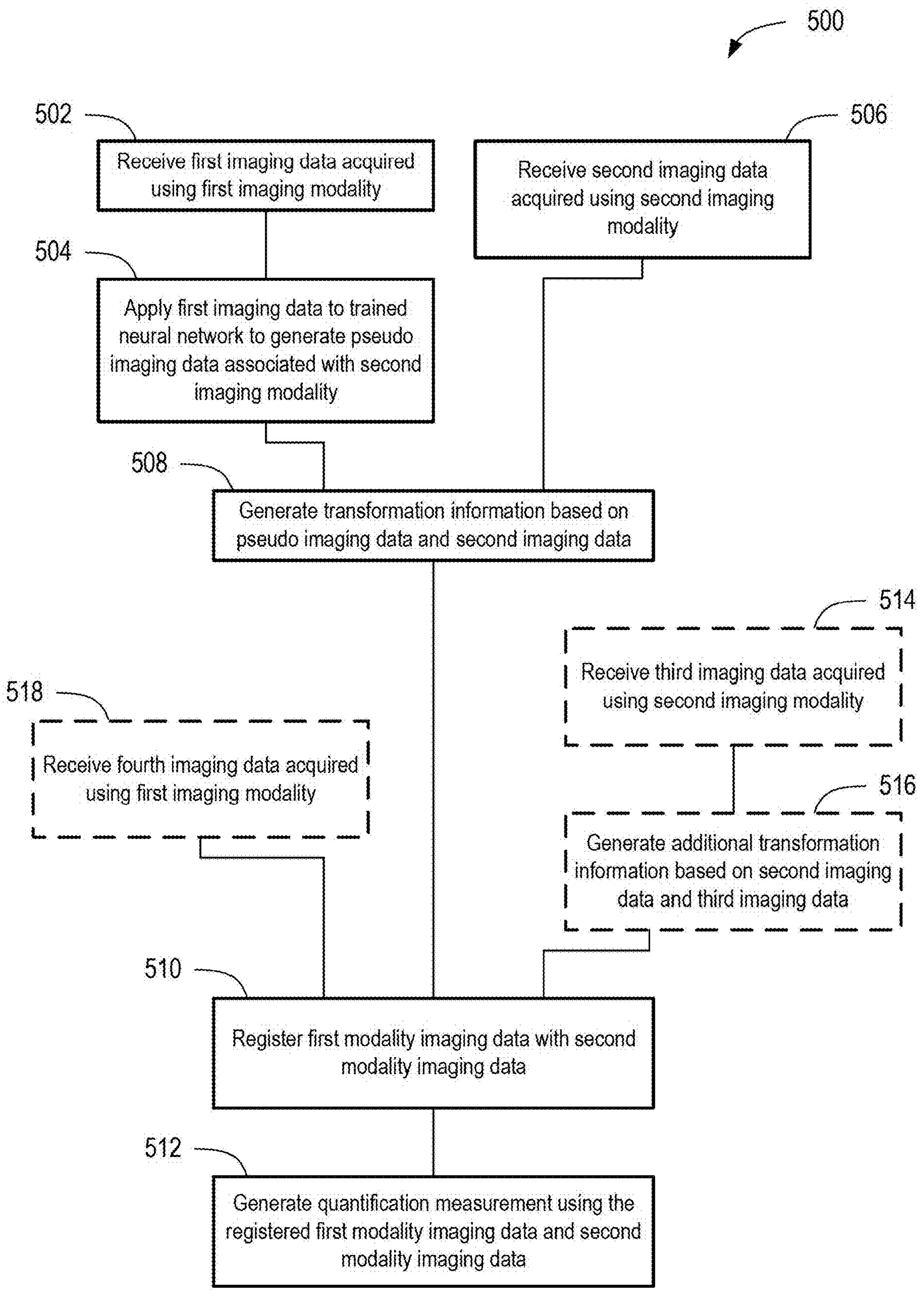
FIG. 5 is a flowchart depicting a process for automatically registering multi-modal imaging data, according to certain aspects of the present disclosure.

FIG. 5 is a flowchart depicting a process 500 for automatically registering multi-modal imaging data, according to certain aspects of the present disclosure. Process 500 can be performed by any computing device or combination of computing devices, such as processing module 114 of FIG. 1 and/or processing module 214 of FIG. 2.

At block 502, first imaging data acquired using a first imaging modality is received. Receiving this imaging data can include receiving the imaging data from an imager (e.g., a PET imager) or from a repository of imaging data (e.g., a memory containing the imaging data).

At block 504, the first imaging data is applied to a trained neural network to generate pseudo imaging data. The pseudo imaging data is associated with a second imaging modality. In other words, the pseudo imaging data is intended to appear as if it were acquired using the second imaging modality. The trained neural network can be a generator neural network of a GAN that has been trained on first modality imaging data and second modality imaging data to generate, from the first modality imaging data, pseudo imaging data that appears to have been acquired using the second imaging modality.

At block 506, second imaging data acquired using a second imaging modality is received. Receiving this imaging data can include receiving the imaging data from an imager (e.g., a CT imager) or from a repository of imaging data (e.g., a memory containing the imaging data).

At block 508, transformation information is generated based on the pseudo imaging data and the second imaging data. More specifically, a registration process can be undertaken to register the pseudo imaging data to the second imaging data. As a result of the registration process, certain transformation information can be obtained. This transformation information can be information indicative of how the pseudo imaging data must be transformed to become registered with the second imaging data. In some cases, the registration process at block 508 is a diffeomorphic non-rigid registration process. The diffeomorphic registration algorithm can be a demons algorithm, which can iteratively compute the displacement for each voxel in a computationally efficient manner.

At block 510, first modality imaging data is registered with second modality imaging data using the transformation information from block 508. In some cases, the first modality imaging data and second modality imaging data are the first imaging data from block 502 and second imaging data from block 506, respectively, although that need not always be the case. In some cases, such as described in further detail with reference to blocks 514, 516, 518, the first modality imaging data is different data that has been acquired in the first imaging modality and the second modality imaging data is different data that has been acquired in the second imaging modality. For example, the first imaging data at block 502 may be NAC PET imaging data, the second imaging data at block 506 can be non-contrast CT AC imaging data, the first modality imaging data can be attenuation corrected PET imaging data, and the second modality imaging data can be CT angiography imaging data.

In some optional cases, third imaging data acquired using the second imaging modality is received at block 514. Receiving this imaging data can include receiving the imaging data from an imager (e.g., a CT imager) or from a repository of imaging data (e.g., a memory containing the imaging data).

At optional block 516, additional transformation information can be generated based on the second imaging data and the third imaging data. More specifically, a registration process can be undertaken to register the second imaging data to the third imaging data. As a result of the registration process, the additional transformation information can be obtained. This additional transformation information can be information indicative of how the second imaging data must be transformed to become registered with the third imaging data.

When optional blocks 514, 516 are used, registering the first modality imaging data with the second modality imaging data at block 510 can include applying both the transformation information from block 508 and the second transformation information from block 516 to the first modality imaging data to register it to the third imaging data from block 514.

In some optional cases, fourth imaging data acquired using the first imaging modality is received at block 518. Receiving this imaging data can include receiving the imaging data from an imager (e.g., a PET imager) or from a repository of imaging data (e.g., a memory containing the imaging data).

When optional block 518 is used, registering the first modality imaging data with the second modality imaging data at block 510 can include applying the transformation information from block 508 (and optionally the second transformation information from block 516) to the fourth imaging data to register it to the second modality imaging data (e.g., the second imaging data or the third imaging data).

After the first modality imaging data has been registered to the second modality imaging data at block 510, quantification measurements can be generated at block 512. Generation of the quantification measurements can include using the registered first modality imaging data and the second modality imaging data. In some cases, generation of the quantification measurements can include establishing a volume of interest using the second modality imaging data, then calculating the quantification measurements from portions of the first modality imaging data that fall within the volume of interest. For example, in some cases CT angiography imaging data is used to determine certain volumes of interest, which can be used to define regions of the co-registered attenuation corrected PET imaging data from which measurements (e.g., $^{18}$F—NaF uptake measurements) can be acquired. These measurements can be used to generate useful information and other measurements, such as SUVmax, TBRmax, and CMA.

While depicted with certain blocks in a certain order, in some cases process 500 can be performed with fewer or additional blocks, and blocks in different orders. For example, in some cases receiving third imaging data at block 514 and receiving fourth imaging data at block 518 can occur simultaneously with block 502 and/or block 504. In another example, blocks 514, 516, 518 can be left out, in which case the first imaging data can be registered to the second imaging data at block 510. In another example, block 512 can be left out and instead process 500 can end with the generation and display of a graphical user interface depicting the registered first modality imaging data and second modality imaging data. In another example, block 512 can be left out and instead process 500 can end with the generation and storing of the registered first modality imaging data and second modality imaging data.

In an example test of the example methods, imaging data from a patient population was randomly divided into training data and test data sets of 139 and 30 patients, respectively. A generator model was trained using a combination of adversarial loss for discriminator and a mean-squared loss between input PET image slices and generated pseudo-CT image slices. The adversarial loss was optimized to ensure the generator produced realistic pseudo-CT slices and the discriminator was unable to distinguish between real and pseudo-CT slices. A conditional GAN was trained for 250 epochs with a learning rate of 0.0001, an input batch size of 8 NAC PET slices of 256×256 voxels. The output pseudo-CT slices were consolidated per patient and used as reference for the final registration.

In the example test, the generated pseudo-CT scan was first registered to a corresponding non-contrast CT AC scan using a nonlinear diffeomorphic registration algorithm. The non-contrast CT AC imaging data was subsequently registered rigidly to CT angiography imaging data. Both of these transforms (e.g., the pseudo-CT to non-contrast CT AC transform and the non-contrast CT AC to CT angiography transform) were applied together, integrating the two motion vector fields from the first step with the second step to PET imaging data thus registering PET imaging data to CT angiography imaging data using the generated pseudo-CT imaging data.

In this example test, $^{18}$F—NaF uptake within coronary plaque activity was measured using the co-registered PET imaging data and CT angiography imaging data. Whole-vessel tubular and tortuous 3-dimensional volumes of interest were automatically extracted from the CT angiography imaging data. These volumes encompass all the main native epicardial coronary vessels and their immediate surroundings (e.g., a 4-mm radius), enabling both per-vessel and per-patient uptake quantification. Within these volumes of interest, maximum standardized uptake values (SUVmax) and target-to-background (TBRmax) values were calculated from the PET imaging data associated with the volumes of interest. TBRmax values were calculated by dividing the coronary SUVmax by the blood-pool activity measured in the right atrium (mean SUV in cylindrical volumes of interest at the level of the right coronary artery ostium: radius 10 mm and thickness 5 mm). CMA was also measured, which quantified the $^{18}$F—NaF activity across the entire coronary vasculature, and which can be a predictor for myocardial infarction. CMA was defined as the integrated activity in the region where standardized uptake values exceeded the corrected background blood pool mean standardized uptake value+2 standard deviations. The per-patient CMA was defined as the sum of the per-vessel CMA values.

In this example test, these quantitative values were obtained for both traditional, manual registration and automatic registration according to certain aspects of the present disclosure. Translation vectors in each of the 3 directions for manual and automatic registered PET were exported from observer-marked vessels per patient.

In the example tests, the study population comprised 169 patients (81.1% men; mean age: 65.3±8.4 years) with 139 used for training and 30 for testing. All participants had advanced stable coronary atherosclerosis with a high burden of cardiovascular risk factors (hypertension: n=101; 60%; hyperlipidemia: n=148; 88%; tobacco use: n=113; 67%) and were on guideline-recommended therapy (statin: n=151; 90%; antiplatelet therapy: n=155; 92%; angiotensin-converting enzyme inhibitor or angiotensin receptor blockers: n=113; 67%) and had high rates of prior revascularization (n=137; 81%).

Twenty-five (83%) of the 30 patients in the testing set had poor registration between NAC PET and non-contrast CT AC, according to expert observer. To achieve perfect alignment of the PET and CT images all datasets in the training dataset required adjustments made by the interpreting physician. These were most prominent in the z-axis reflecting the discordance in the diaphragm position-which is a result of breathing (while CT AC data can be acquired during a breath-hold the PET scan lasts for 30 minutes).

A single case example of GAN-based nonlinear diffeomorphic registration (e.g., automatic registration according to certain aspects of the present disclosure) was reviewed, showing similar registration and SUVmax in the coronary arteries compared to an expert observer (e.g., manual registration). Activity of 88 vessels in the 30 patients, was assessed using TBRmax, SUVmax, and CMA. The TBRmax had a coefficient of repeatability (CR) of 0.31, a mean bias of 0.02, and narrow limits of agreement (LOA) (95% LOA—0.29 to 0.33). The SUVmax had an excellent CR of 0.26, a mean bias of 0, and narrow limits of agreement (95% LOA—0.26 to 0.26). Between observer and GAN-based registration, the CMA had CR of 0.57, a mean bias of 0.03, and narrow limits of agreement (95% LOA—0.54 to 0.60). Difference in displacement motion vectors between GAN and observer-based registration was 0.8±3.02 mm in the x-direction, 0.68±2.98 mm in the y-direction, and 1.66±3.94 mm in the z-direction. The overall time for the GAN-based registration with analysis was 84 seconds on a CPU workstation and 27.5 seconds on a GPU workstation. The overall registration and analysis time for the experienced observer was 15±2.5 minutes.

Figure 6:
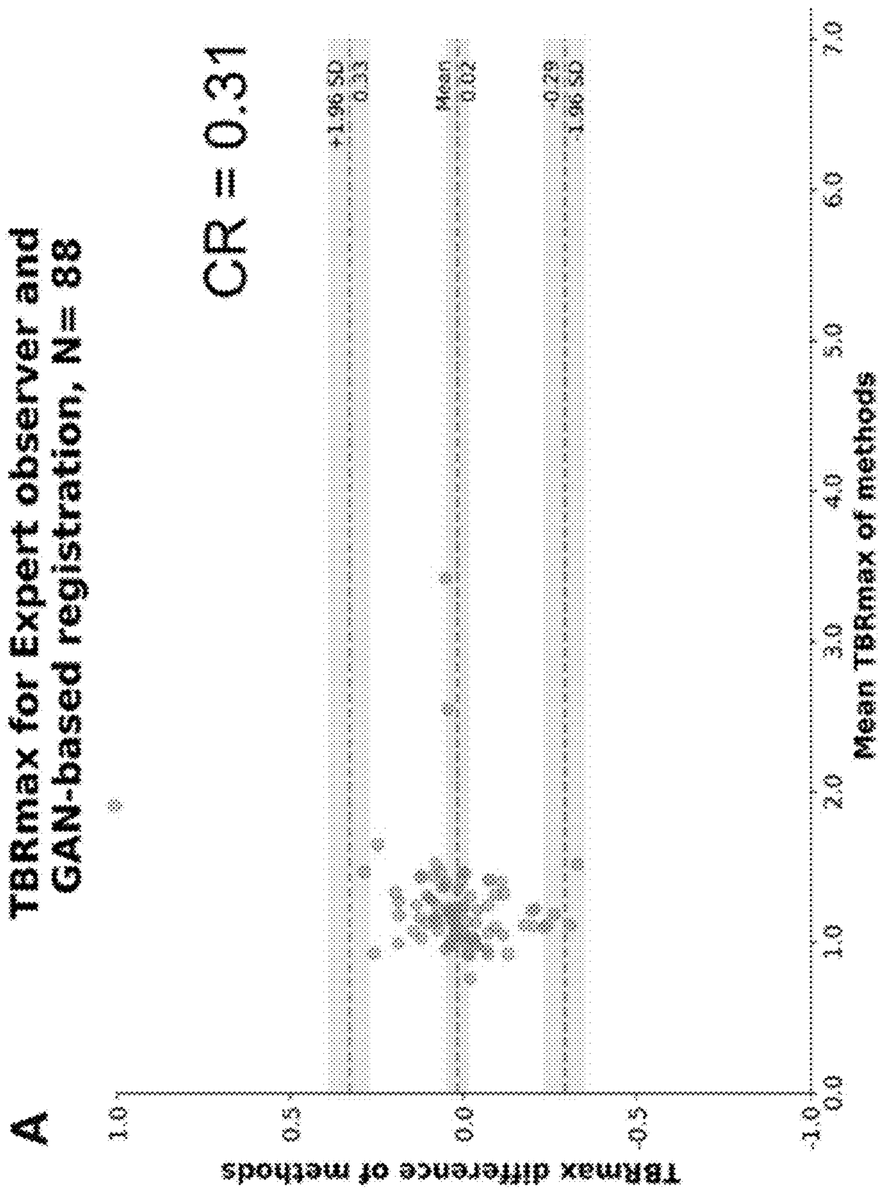
FIG. 6 is a chart comparing example maximal target-to-background ratios as obtained from manual registration and automatic registration, according to certain aspects of the present disclosure.

FIG. 6 is a chart 600 comparing example maximal target-to-background (TBRmax) ratios as obtained from manual registration and automatic registration of the example test subjects, according to certain aspects of the present disclosure. The chart 600 is a Bland-Altman plot of observer (e.g., manual registration) and GAN-based nonlinear diffeomorphic registration (e.g., automatic registration as disclosed herein) measurements of maximal target-to-background ratio (TBRmax) values at vessel level.

The TBRmax ratios depicted in FIG. 6 are based on the example test described above for 88 vessels of 30 patients. As explained above, the TBRmax had a coefficient of repeatability (CR) of 0.31, a mean bias of 0.02, and narrow limits of agreement (LOA) (95% LOA—0.29 to 0.33).

Figure 7:
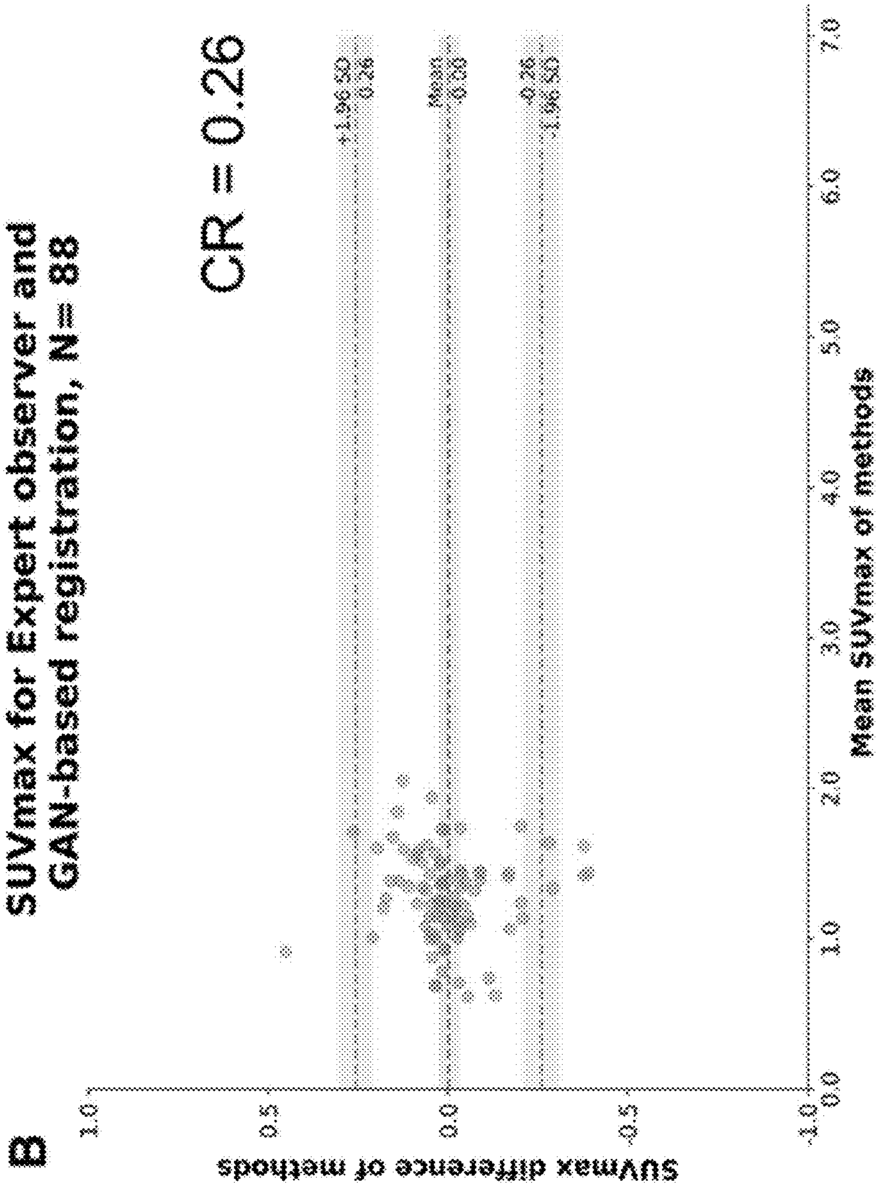
FIG. 7 is a chart comparing example maximal standardized uptake values as obtained from manual registration and automatic registration, according to certain aspects of the present disclosure.

FIG. 7 is a chart 700 comparing example standardized uptake values (SUV) as obtained from manual registration and automatic registration of the example test subjects, according to certain aspects of the present disclosure. The chart 700 is a Bland-Altman plot of observer (e.g., manual registration) and GAN-based nonlinear diffeomorphic registration (e.g., automatic registration as disclosed herein) measurements of maximal standard uptake value (SUVmax) at vessel level.

The SUVmax values depicted in FIG. 7 are based on the example test described above for 88 vessels of 30 patients. SUVmax had excellent CR of 0.26, mean bias of 0, and narrow limits of agreement (95% LOA—0.26 to 0.26).

Figure 8:
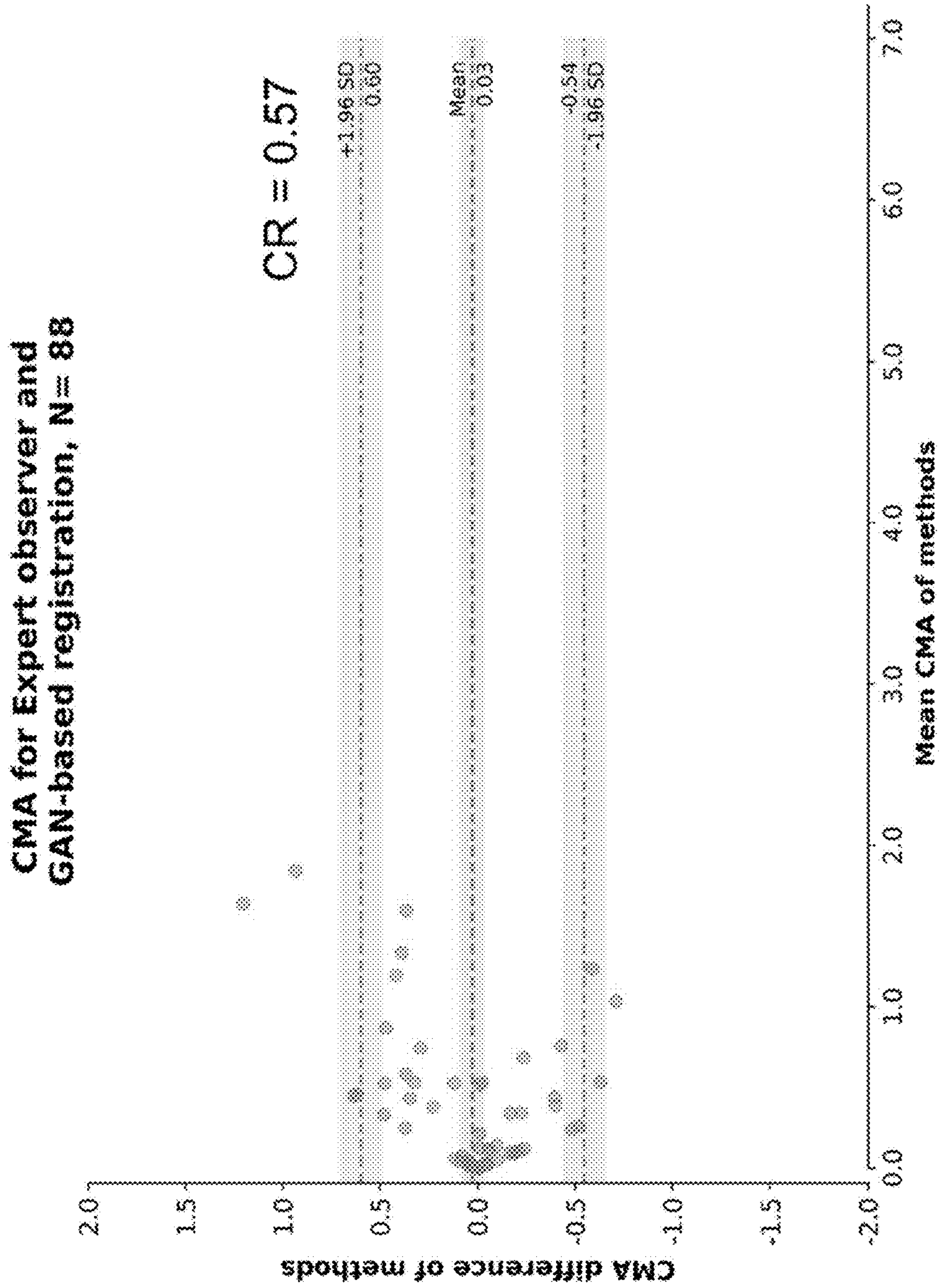
FIG. 8 is a chart comparing example coronary microcalcification activity values as obtained from manual registration and automatic registration, according to certain aspects of the present disclosure.

FIG. 8 is a chart 800 comparing example coronary microcalcification activity (CMA) values as obtained from manual registration and automatic registration of the example test subjects, according to certain aspects of the present disclosure. The chart 800 is a Bland-Altman plot of observer (e.g., manual registration) and GAN-based nonlinear diffeomorphic registration (e.g., automatic registration as disclosed herein) measurements of coronary microcalcification activity (CMA) at vessel level.

The CMA values depicted in FIG. 8 are based on the example test described above for 88 vessels of 30 patients. Between observer and GAN-based registration, CMA had CR of 0.57, mean bias of 0.03, and narrow limits of agreement (95% LOA—0.54 to 0.60).

Figure 9:
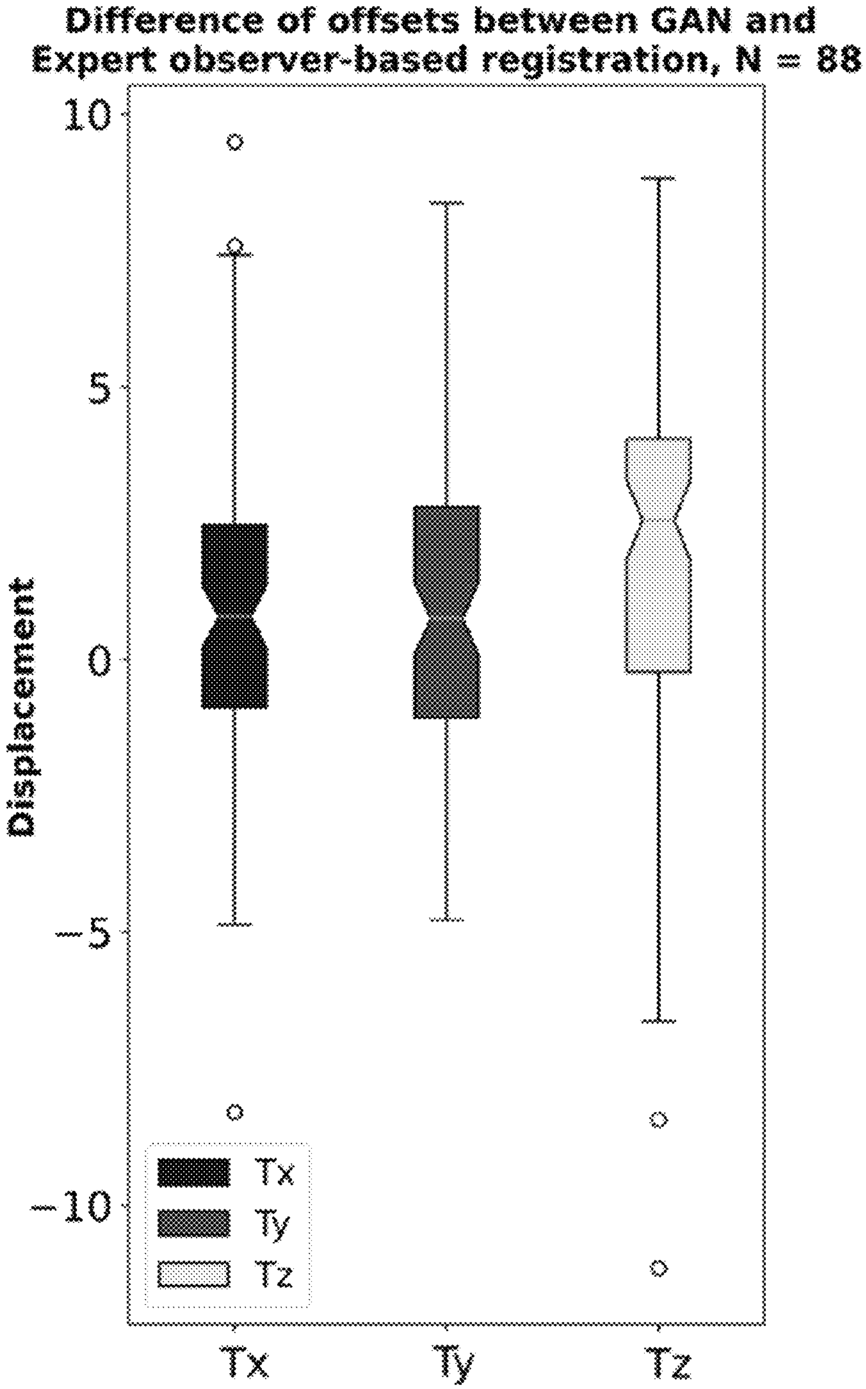
FIG. 9 is a chart depicting examples of the difference of offsets between manual registration and automatic registration, according to certain aspects of the present disclosure.

FIG. 9 is a chart 900 depicting examples of the difference of offsets between manual registration and automatic registration, according to certain aspects of the present disclosure. The chart 900 depicts displacement differences in x-, y-, and z-directions between observer (e.g., manual registration) and GAN-based nonlinear diffeomorphic registration (e.g., automatic registration as disclosed herein). The displacement differences are measured at the vessel level in mm, in the location of the quantified vessels.

The displacement difference values depicted in FIG. 9 are based on the example case described above for 88 vessels of 30 patients. Difference in displacement motion vectors between GAN and observer-based registration was 0.8±3.02 mm in the x-direction, 0.68±2.98 mm in the y-direction, and 1.66±3.94 mm in the z-direction.

Figure 10:
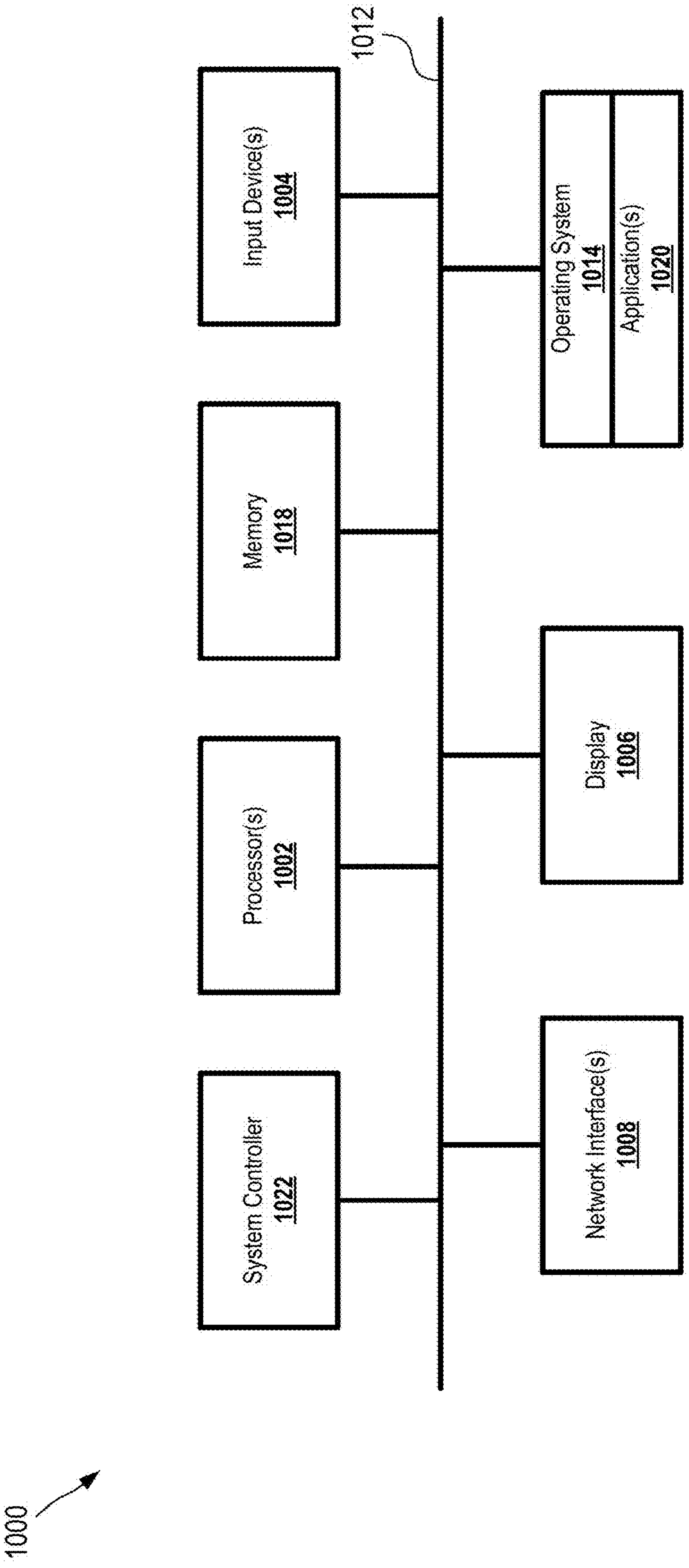
FIG. 10 is a block diagram of an example system architecture for implementing features and processes of the present disclosure.

FIG. 10 is a block diagram of an example system architecture 1000 for implementing features and processes of the present disclosure, such as those presented with reference to FIG. 1-9. The system architecture 1000 can be used to implement any suitable computing device (e.g., a server, workstation, tablet, imager, imaging data processing module, or other such device) for practicing the various features and processes of the present disclosure. The system architecture 1000 can be implemented on any electronic device that runs software applications derived from compiled instructions, including without limitation personal computers, servers, smart phones, electronic tablets, game consoles, email devices, and the like. In some implementations, the system architecture 1000 can include one or more processors 1002, one or more input devices 1004, one or more display devices 1006, one or more network interfaces 1008, and memory 1018 (e.g., one or more computer-readable mediums). Each of these components can be coupled by bus 1012.

In some cases, system architecture 1000 can be incorporated into a computing system capable of performing SPECT imaging and/or PET imaging, such as a computing system used to control SPECT and/or PET imagers. In some cases, system architecture 1000 can be incorporated into a workstation computer used primarily for viewing and interpreting imaging data, such as a workstation located in the office of a medical professional interpreting the imaging data acquired at a different location (e.g., a different facility).

Display device 1006 can be any known display technology, including but not limited to display devices using Liquid Crystal Display (LCD) or Light Emitting Diode (LED) technology. Processor(s) 1002 can use any known processor technology, including but not limited to graphics processors and multi-core processors. Input device 1004 can be any known input device technology, including but not limited to a keyboard (including a virtual keyboard), mouse, track ball, and touch-sensitive pad or display. Bus 1012 can be any known internal or external bus technology, including but not limited to ISA, EISA, PCI, PCI Express, NuBus, USB, Serial ATA, or FireWire.

Computer-readable medium can be any medium that participates in providing instructions to processor(s) 1002 for execution, including without limitation, non-volatile storage media (e.g., optical disks, magnetic disks, flash drives, etc.) or volatile media (e.g., SDRAM, ROM, etc.). The computer-readable medium (e.g., storage devices, mediums, and memories) can include, for example, a cable or wireless signal containing a bit stream and the like. However, when mentioned, non-transitory computer-readable storage media expressly exclude media such as energy, carrier signals, electromagnetic waves, and signals per se.

Computer-readable medium can include various instructions for implementing operating system 1014 and applications 1020 such as computer programs. The operating system can be multi-user, multiprocessing, multitasking, multithreading, real-time and the like. The operating system 1014 performs basic tasks, including but not limited to: recognizing input from input device 1004; sending output to display device 1006; keeping track of files and directories on computer-readable medium; controlling peripheral devices (e.g., disk drives, printers, etc.) which can be controlled directly or through an I/O controller; and managing traffic on bus 1012. Computer-readable medium can include various instructions for implementing firmware processes, such as a BIOS. Computer-readable medium can include various instructions for implementing any of processes described herein, including at least process 500 of FIG. 5.

Memory 1018 (e.g., the computer-readable medium) can include high-speed random access memory and/or non-volatile memory, such as one or more magnetic disk storage devices, one or more optical storage devices, and/or flash memory (e.g., NAND, NOR). The memory 1018 (e.g., computer-readable storage devices, mediums, and memories) can include a cable or wireless signal containing a bit stream and the like. However, when mentioned, non-transitory computer-readable storage media expressly exclude media such as energy, carrier signals, electromagnetic waves, and signals per se. The memory 1018 can store an operating system, such as Darwin, RTXC, LINUX, UNIX, OS X, WINDOWS, or an embedded operating system such as VxWorks.

System controller 1022 can be a service processor that operates independently of processor 1002. In some implementations, system controller 1022 can be a baseboard management controller (BMC). For example, a BMC is a specialized service processor that monitors the physical state of a computer, network server, or other hardware device using sensors and communicating with the system administrator through an independent connection. The BMC is configured on the motherboard or main circuit board of the device to be monitored. The sensors of a BMC can measure internal physical variables such as temperature, humidity, power-supply voltage, fan speeds, communications parameters, and operating system (OS) functions.

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., Objective-C, Java, Python), including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computing system that includes a back-end component, such as a data server, or that includes a middleware component, such as an application server or an Internet server, or that includes a front-end component, such as a client computer having a graphical user interface or an Internet browser, or any combination thereof. The components of the system can be connected by any form or medium of digital data communication such as a communication network. Examples of communication networks include, e.g., a LAN, a WAN, and the computers and networks forming the Internet.

The computing system can include clients and servers. A client and server are generally remote from each other and typically interact through a network. The relationship of client and server arises by virtue of computer programs running on the respective computers and having a client-server relationship to each other.

One or more features or steps of the disclosed embodiments can be implemented using an application programming interface (API). An API can define one or more parameters that are passed between a calling application and other software code (e.g., an operating system, library routine, function) that provides a service, that provides data, or that performs an operation or a computation.

The API can be implemented as one or more calls in program code that send or receive one or more parameters through a parameter list or other structure based on a call convention defined in an API specification document. A parameter can be a constant, a key, a data structure, an object, an object class, a variable, a data type, a pointer, an array, a list, or another call. API calls and parameters can be implemented in any programming language. The programming language can define the vocabulary and calling convention that a programmer will employ to access functions supporting the API.

In some implementations, an API call can report to an application the capabilities of a device running the application, such as input capability, output capability, processing capability, power capability, communications capability, and the like.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art. Numerous changes to the disclosed embodiments can be made in accordance with the disclosure herein, without departing from the spirit or scope of the disclosure. Thus, the breadth and scope of the present disclosure should not be limited by any of the above described embodiments.

Although certain aspects and features of the present disclosure have been illustrated and described with respect to one or more implementations, equivalent alterations and modifications will occur or be known to others skilled in the art upon the reading and understanding of this specification and the annexed drawings. In addition, while a particular feature may have been disclosed with respect to only one of several implementations, such feature may be combined with one or more other features of the other implementations as may be desired and advantageous for any given or particular application.

The terminology used herein is for the purpose of describing particular embodiments only, and is not intended to be limiting of the disclosure. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

One or more elements or aspects or steps, or any portion(s) thereof, from one or more of any of the claims below can be combined with one or more elements or aspects or steps, or any portion(s) thereof, from one or more of any of the other claims or combinations thereof, to form one or more additional implementations and/or claims of the present disclosure.

What is claimed is:

1. A computer-implemented method, comprising:

receiving first imaging data of a subject, the first imaging data acquired using a first imaging modality;

applying the first imaging data to a neural network trained to output pseudo imaging data, the pseudo imaging data associated with a second imaging modality;

receiving second imaging data of the subject, the second imaging data acquired using the second imaging modality;

receiving transformation information based at least in part on the pseudo imaging data and the received second imaging data;

registering first modality imaging data with second modality imaging data by applying the transformation information;

receiving third imaging data of the subject, the third imaging data acquired using the second imaging modality; and generating additional transformation information based at least in part on a comparison of the second imaging data and the third imaging data, wherein registering the first modality imaging data with the second modality imaging data further includes applying the additional transformation information, wherein the second modality imaging data is the third imaging data.

2. The method of claim 1, wherein the first modality imaging data is the first imaging data and the second modality imaging data is the second imaging data.

3. The method of claim 1, wherein the first imaging modality is positron emission tomography (PET) and the second imaging modality is computed tomography (CT).

4. The method of claim 1, wherein the second imaging data is non-contrast computed tomography attenuation correction imaging data.

5. The method of claim 1, wherein the first imaging data is $^{18}$F—Na—F positron emission tomography imaging data.

6. The method of claim 5, wherein the $^{18}$F—Na—F positron emission tomography imaging data is non-attenuation-corrected $^{18}$F—Na—F positron emission tomography imaging data.

7. The method of claim 1, wherein the first modality imaging data is attenuation corrected $^{18}$F—Na—F positron emission tomography imaging data.

8. The method of claim 7, wherein the second modality imaging data is computed tomography angiography imaging data.

9. The method of claim 1, wherein the subject includes coronary tissue.

10. The method of claim 1, wherein receiving the transformation information includes generating the transformation information by applying a diffeomorphic registration algorithm to the pseudo imaging data and the second imaging data.

11. The method of claim 1, wherein the neural network includes a generator neural network of a generative adversarial network (GAN), the generator neural network trained to receive first training data associated with the first imaging modality as input and output generated imaging data associated with the second imaging modality.

12. The method of claim 11, wherein the GAN is a conditional GAN having at least one condition, wherein the at least one condition is a slice label associated with the training data, wherein each image slice of the training data is associated with a respective slice label.

13. The method of claim 1, wherein applying the first imaging data to the neural network to output the pseudo imaging data includes individually applying image slices of the first imaging data to the neural network to output corresponding pseudo imaging slices of the pseudo imaging data.

14. The method of claim 1, wherein the first imaging data is nonattenuation corrected positron emission tomography imaging data; wherein the second imaging data is non-contrast computed tomography attenuation correction imaging data; and wherein the third imaging data is computed tomography angiography imaging data.

15. The method of claim 1, further comprising receiving fourth imaging data of the subject, the fourth imaging data acquired using the first imaging modality, wherein the first modality imaging data is the fourth imaging data.

16. The method of claim 15, wherein the fourth imaging data is attenuation corrected positron emission tomography imaging data.

17. The method of claim 1, further comprising:

identifying one or more regions of interest of the subject based at least in part on the second modality imaging data; and generating a quantification measurement based at least in part on the first modality imaging data and the identified one or more regions.

18. A system, comprising:

one or more data processors; and a non-transitory computer-readable storage medium containing instructions which, when executed on the one or more data processors, cause the one or more data processors to perform:

receiving first imaging data of a subject, the first imaging data acquired using a first imaging modality;

applying the first imaging data to a neural network trained to output pseudo imaging data, the pseudo imaging data associated with a second imaging modality;

receiving second imaging data of the subject, the second imaging data acquired using the second imaging modality;

receiving transformation information based at least in part on the pseudo imaging data and the received second imaging data;

registering first modality imaging data with second modality imaging data by applying the transformation information;

receiving third imaging data of the subject, the third imaging data acquired using the second imaging modality; and generating additional transformation information based at least in part on a comparison of the second imaging data and the third imaging data, wherein registering the first modality imaging data with the second modality imaging data further includes applying the additional transformation information, wherein the second modality imaging data is the third imaging data.

19. A computer-program product tangibly embodied in a non-transitory machine-readable storage medium, including instructions configured to cause a data processing apparatus to perform:

receiving first imaging data of a subject, the first imaging data acquired using a first imaging modality;

applying the first imaging data to a neural network trained to output pseudo imaging data, the pseudo imaging data associated with a second imaging modality;

receiving second imaging data of the subject, the second imaging data acquired using the second imaging modality;

receiving transformation information based at least in part on the pseudo imaging data and the received second imaging data;

registering first modality imaging data with second modality imaging data by applying the transformation information;

receiving third imaging data of the subject, the third imaging data acquired using the second imaging modality; and generating additional transformation information based at least in part on a comparison of the second imaging data and the third imaging data, wherein registering the first modality imaging data with the second modality imaging data further includes applying the additional transformation information, wherein the second modality imaging data is the third imaging data.

* * * * *